United States Patent [19]

Cuzzato et al.

[11] Patent Number: 4,814,113
[45] Date of Patent: Mar. 21, 1989

[54] PROCESS FOR THE PREPARATION OF PERFLUOROACYL FLUORIDES

[75] Inventors: Paolo Cuzzato; Arsenio Castellan; Antonio Pasquale, All of Novara, Italy

[73] Assignee: Ausimont S.p.A., Milan, Italy

[21] Appl. No.: 98,469

[22] Filed: Sep. 18, 1987

[30] Foreign Application Priority Data

Sep. 19, 1986 [IT] Italy .................. 21758 A/86
Dec. 14, 1986 [IT] Italy .................. 22863 A/86

[51] Int. Cl.$^4$ .............................................. C07C 51/62
[52] U.S. Cl. ..................................................... 260/544 F
[58] Field of Search ..................................... 260/544 F

[56] References Cited

U.S. PATENT DOCUMENTS

| | | | |
|---|---|---|---|
| 2,439,505 | 4/1948 | Chaney | 260/544 F |
| 3,291,843 | 12/1966 | Fritz | 260/544 F |
| 3,536,733 | 10/1970 | Carlson | 260/544 F |
| 4,350,750 | 7/1982 | Yamabe | 260/544 F |
| 4,524,031 | 6/1985 | Millauer | 260/544 F |
| 4,590,015 | 5/1986 | Resnick | 260/544 F |
| 4,597,913 | 7/1986 | Kimoto | 260/544 F |

*Primary Examiner*—Paul J. Killos
*Attorney, Agent, or Firm*—Stevens, Davis, Miller & Mosher

[57] ABSTRACT

Process for the preparation of a perfluoroacyl fluoride wherein the acyl radical is a propionyl or butyryl group, characterized in that perfluoroalkylvinylether wherein the alkyl radical is a methyl or ethyl group is thermally treated in the presence of a catalyst selected from the group consisting of:

(A) a fluoride of Li, Na, K, Cs or Rb, or another compound of Li, Na, K, Cs or Rb which is easily fluorinated under the reaction conditions;

(B) a fluoride of Be, Mg, Ca, Sr, or Ba, or another compound of Be, Mg, Ca, Sr, or Ba which is easily fluorinatable under the reaction conditions:

(C) a fluoroaluminate, fluorosilicate, fluorotitanate or fluorometallate of an alkali metal, or of a metal belonging to group IIA of the Periodic Table, i.e., compounds consisting of fluorine, an alkali metal and a transition metal, or a compound which is easily fluorinatable to yield one of the above-said fluoroaluminates, fluorosilicates, fluorotitanates or fluorometallates under the reaction conditions;

(D) a fluoride of a metal of the first transition series, or the corresponding metal, or another compound of such a metal which is easily fluorinatable under the reaction conditions;

(E) a fluoride of a lathanide or the corresponding metal, or another compound of such a metal which is easily fluorinatable under the reaction conditions; and (F) an oxyfluoride of Si, Al, Ti, Ge, Sn or Pb, or another compound of Si, Al, Ti, Ge, Sn or Pb which is easily fluorinatable to yield one of the above-said oxyfluorides under the reaction conditions.

26 Claims, No Drawings

PROCESS FOR THE PREPARATION OF PERFLUOROACYL FLUORIDES

DESCRIPTION OF THE INVENTION

The present invention relates to a process for the preparation of perfluoroacyl fluorides wherein the acyl radical is a propionyl or butyryl group.

The perfluoroacyl fluorides are intermediate products which are of considerable interest from the commercial viewpoint. They can be used, e.g., for the purpose of obtaining water-repellent and oil-repellent products on paper and fabrics, for the preparation of surface-active agents, of flame-proofing agents, and for the production of emulsifing agents for the polymerization of fluorinated olefins in aqueous medium.

The perfluoroacyl fluorides may be obtained by various methods, among which are electrochemical fluorination of the carboxylic acids or of their derivatives (chlorides, esters), and by starting from iodoperfluoroalkanes.

As reported in the treatise by R. E. Banks, "Preparation, Properties and Industrial Applications of Organofluorine Compounds", Chapter 1, Ellis Horwood Ltd., Chichester, 1982, these processes are in general expensive, they do not allow high yields and high purities to be achieved as in the case of electrochemical fluorination, or they require many steps and start from expensive starting materials, as in the case of starting from iodoperfluoroalkanes.

The purity is an essential requirement in perfluoroacyl fluorides, in that its lack can prevent the use of these intermediate products in subsequent conversion reactions wherein a high purity is required, such as, e.g., in the conversion into perfluoroalkyl-fluorooxy-compounds which are known to give rise to explosive decompositions, initiated by traces of impurities.

R. N. Hazeldine and A. E. Tipping (J. Chem. Soc. (C), 398-405, 1968), report a reaction of pyrolytic rearrangement of trifluoromethyltrifluorovinylether at 595° C., inside a platinum reactor. This reaction causes the formation of several products, among which is perfluoropropionyl fluoride, this latter product being obtained with a yield of 53%.

An object of the present invention is that of supplying a process for the preparation of perfluoroacyl fluorides, wherein the acyl radical is a propionyl or butyryl group, which gives high yields and a high selectivity.

Another object is that of supplying very pure products, rendering needless or at least reducing to the very minimum the operations of purification, and thus avoiding the risks connected with instability, e.g., to hydrolysis, of such products.

These and still further objects are achieved by the process of the present invention for the preparation of perfluoroacyl fluorides, wherein the acyl radical is a propionyl or butyryl group. This process is characterized in that a perfluoroalkylvinylether wherein the alkyl radical is a methyl or an ethyl group, is thermally treated in the presence of a catalyst selected from the group consisting of:

(A) a fluoride of Li, Na, K, Cs or Rb, or another compound of Li, Na, K, Cs or Rb which is easily fluorinatable under the reaction conditions;

(B) a fluoride of Be, Mg, Ca, Sr, or Ba, or another compound of Be, Mg, Ca, Sr, or Ba which is easily fluorinatable, under the reaction conditions;

(C) a fluoroaluminate, fluorosilicate, fluorotitanate or fluorometallate of an alkali metal, or of a metal belonging to group IIA of the Periodic Table, i.e., compounds consisting of fluorine, an alkali metal and a transition metal, or another compound which is easily fluorinatable to yield one of the above said fluoroaluminates, fluorosilicates, fluorotitanates or fluorometallates under the reaction conditions;

(D) a fluoride of a metal of the first transition series (i.e., of the metals having an atomic number of from 21 to 30), or the corresponding metal, or another compound of such a metal which is easily fluorinatable under the reaction conditions;

(E) a fluoride of a lanthanide, or the corresponding metal, or another compound of such a metal which is easily fluorinatable under the reaction conditions; and (F) an oxyfluoride of Si, Al, Ti, Ge, Sn or Pb, or another compund of Si, Al, Ti, Ge, Sn or Pb which is easily fluorinatable to yield one of the above-said oxyfluorides under the reaction conditions.

The reaction is the following:

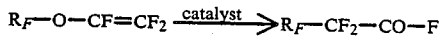

$$R_F\text{—}O\text{—}CF\text{=}CF_2 \xrightarrow{\text{catalyst}} R_F\text{—}CF_2\text{—}CO\text{—}F$$

wherein $R_F$ is either $CF_3$ or $C_2F_5$.

The metals and the other easily fluorinatable compounds used as catalysts form in situ, under the reaction conditions, fluorinated species, under the action of the perfluoroalkylvinylether. They can also be fluorinated before carrying out the reaction by means of another reactant capable of fluorinating them, e.g., fluorine or hydrofluoric acid.

Among the compounds of Li, Na, K, Cs and Rb which are easily fluorinatable under the reaction conditions, the oxides, the hydrooxides and the oxyhalides, e.g., $Li_2O$, $Na_2O$, $K_2O$, $Cs_2O$, LiOH, NaOH, KOH, CsOH, oxychlorites of Li, Na, K and Cs may be mentioned.

Among the compounds of Be, Mg, Ca, Sr and Ba which are easily fluorinatable under the reaction conditions, the oxides, the hydroxides and the oxyhalides, e.g., BaO, MgO, CaO, SrO, $Ba(OH)_2$, $Mg(OH)_2$, $Ca(OH)_2$, $Sr(OH)_2$, $Ba(OCl)_2$, oxychlorites of Ba, Mg, Ca, Sr may be mentioned.

Among the fluoroaluminates, fluorosilicates, fluorotitanates and fluorometallates of alkali metals, or of the metals belonging to group IIA of the Periodic Table, for example $K_3AlF_6$, $Cs_3AlF_6$, $K_2SiF_6$, $Cs_2SiF_6$, $CsCuF_3$, $KCuF_3$, $CsNiF_3$ may be mentioned. The preferred compounds in this category are $K_3AlF_6$, $Cs_3AlF_6$, $K_2SiF_6$ and $Cs_2SiF_6$.

Among the compounds which are easily fluorinatable to yield one of the above said fluoroaluminates, fluorosilicates, fluorotitanates or fluorometallates under the reaction conditions, e.g., are the aluminates, the silicates and the titanates of the alkali metals, and of the metals belonging to Group IIA, e.g., $Na_2Al_2O_4$, $Na_2SiO_3$, $K_2Al_2O_4$, $MgAl_2O_4$ and $Na_2TiO_3$, may be mentioned. Also the mixed oxides of the alkali metals, or of the metals of Group IIA with other metals, such as Cu, Zn and Mg, e.g., MgO.CuO, MgO.ZnO, $K_2O$.CuO and $Cs_2O$.MgO, may be mentioned.

Among the fluorides of the metals of the first transition series, e.g., the following may be mentioned: $CuF_2$, $NiF_2$, $ZnF_2$, $CoF_2$, $CoF_3$, $CrF_3$, $MnF_2$, $FeF_2$ and $FeF_3$. Among the corresponding metals, for example, Cu, Ni, Zn, Cr, Mn, Fe and Co may be mentioned; from these latter, Cu, Ni, Zn and Fe are preferred. Most preferred is Cu. Among the other compounds of such metals which are easily fluorinatable under the reaction conditions, e.g., the oxides, such as $Fe_2O_3$, CuO, NiO, $Cr_2O_3$, $Co_2O_3$, $Cu_2Cr_2O_4$; the hydroxides, such as FeO(OH), $Cu(OH)_2$, $Ni(OH)_2$, CrO(OH), CoO(OH) and the oxyhalides, such as FeOCl, Ni(OH)Cl, CrOCl, Cu(OH)Cl, Co(OH)Cl, may be mentioned.

Among the lanthanide fluorides, for example, $LaF_3$ and $CeF_4$ may be mentioned. Among the corresponding metals, lanthanum may be mentioned. Among the other lanthanide compounds which are easily fluorinatable under the reaction conditions, e.g., the oxides, such as $La_2O_3$ and $CeO_2$; the oxide-hydroxides, such as LaO(OH) and $CeO(OH)_2$; the hydroxides, such as $La(OH)_3$ and $Ce(OH)_4$; and the oxyhalides, such as LaOCl and $CeOCl_2$, may be mentioned.

Among the oxyfluorides of Si, Al, Ti, Ge, Sn and Pb, $SiO_xF_y$, wherein $2x+y=4$, is preferred. Among the other compounds which are easily fluorinatable to yield the above-said oxyfluorides, the oxides, such as $SiO_2$, $Al_2O_3$ and $TiO_2$; and the oxide-hydroxides, such as $SiO_x(OH)_y$, with $2x+y=4$; and $AlO_x(OH)_y$, with $2x+y=3$, may be mentioned.

Instead of the metals of the first transition series, or the lanthanides, their alloys, e.g., with steel, brass or bronze, may be used.

Among the pre-formed fluorinated catalysts, the most preferred is $MgF_2$.

When a pre-formed fluoride is used as the starting material, it is often convenient to activate it in situ in the presence of the reactant itself, i.e., the perfluoroalkylvinylether.

When as the starting material a metal, or a non-fluorinated compound, is used, the treatment with the reactant itself is necessary and may lead both to the formation of fluorinated species, and to the at least partial activation of the starting material. Instead of the reactant itself another fluorinating agent, such as, e.g., $F_2$ or HF, may be used, leading to the formation of fluorides and to the at least partial activation of the raw material used.

Before subjecting the metal, or the non-fluorinated compound, to the treatment of fluorination and activation, it is preferably first subjected to a thermal treatment. This thermal treatment is generally carried out at temperatures within the range of from 300° to 650° C. in the case of metals, and from 250° to 500° C., in the case of the fluorinatable compounds, compatibly with their chemical and physical stability. Usually, the duration of such thermal treatment is within the range of fom 1 to 3 hours.

Also an already fluorinated catalyst may be thermally activated. This activation is generally carried out at the same temperature at which the reaction takes place, or at higher temperatures.

The temperature range within which the reaction may be carried out varies according to the catalyst and may depend upon its chemical nature, its physical shape, and its degree of activation.

In general, the conversion tends to increase with increasing temperatures, while the selectivity increases up to certain values of temperature, and then decreases at higher temperatures. For each catalyst, a range of temperatures hence exists within which good results are obtained, and a narrower range exists, within which the best combination of conversion and selectivity is achieved, for the obtainment of high yields of the desired perfluoroacyl fluoride.

With the metals of the first transition series, good results are generally obtained within the range of from 300° to 500° C., while the best results are commonly obtained at temperatures of from 350° to 450° C. in he case of Cu, Ni, Zn and Fe.

With the oxyfluorides of Si, Al, Ti, Ge, Sn and Pb, and the other compounds of Si, Al, Ti, Ge, Sn and Pb which are easily fluorinatable to yield the above-said oxyfluorides under the reaction conditions, good results are generally obtained at temperatures of from 250° to 400° C., while the best results are obtained at temperatures of from 300° to 400° C. in the case of fluorinated silica.

With the fluorides of Be, Mg, Ca, Sr and Ba, and the other compounds of Be, Mg, Ca, Sr and Ba which are easily fluorinatable under the reaction conditions, good results are generally obtained at temperatures of from 300° to 450° C., with the best results being obtained from 350° to 450° C. in the case of $MgF_2$.

With the fluorides of Li, Na, K, Cs and Rb and the other compounds of Li, Na, K, Cs and Rb which are easily fluorinatable under the reaction conditions, good results are generally obtained at temperatures within the range of from 300° to 450° C.; in the case of KF, the preferred operating range is from 320° to 360° C.

The optimum activation temperature and time vary from catalyst to catalyst. In general, the activation is faster with increasing temperatures. In case of a pre-formed catalyst, the activation is commonly carried out at the same temperatures at which the reaction is carried out. Also the fluorination and activation of a metal, or of a fluorinatable compound, usually takes place at the same temperatures at which the reaction is carried out.

The granulometry and the physical shape of the catalyst are not critical. The catalyst is commonly used with a granulometry within the range of from 250 microns to 2 mm. When the catalyst is a metal, it may be in the form of filaments, chips, needles, and so forth, having dimensions of a few mm. The metal surface can be smooth, or it can show a certain degree of porosity, with a specific surface area, e.g., within the range of from 0.05 to 0.1 $m^2/g$.

Fluorinated catalysts in admixture with metals may be used as well. Such metals may be both metals which, by fluorination, yield catalysts in accordance with the present invention, e.g., Cu and Ni, and other metals, e.g., Al. The presence of the metal helps to remove from the reaction medium.

As an alternative, the fluorinated catalyst may be supported on the metal material. A method of preparation of a fluorinated catalyst supported on copper consists in subjecting a copper oxide (CuO or $Cu_2O$ or a mixture thereof), in the shape of filaments or needles or granules having a diameter within the range of from 250 microns to 2 mm, to reduction with hydrogen diluted with nitrogen, at a temperature of from 250° to 350° C., a catalyst support being thus obtained which is constituted by metal copper in porous form, having a specific surface area, e.g., of from 0.05 to 0.1 $m^2/g$. This support is then impregnated with a solution (e.g., an aqueous or alcoholic solution) of a fluoride, e.g., NaF. Finally, the solvent used is evaporated off under vacuum.

In the process of the present invention, either a single catalyst or a mixture of catalysts may be used.

The process may be carried out batchwise or, preferably, continuously. When the process is carried out batchwise, the reaction may be carried out in an autoclave, operating under the endogenous pressure developed by the system.

Preferably, the process is carried out continuously, by flowing a stream of perfluoalkylvinylether in gas phase through or over the catalyst bed.

The perfluoroalkylvinylether may be used alone, or in admixture with a gaseous diluent inert under the reaction conditions, e.g., $N_2$, He, or $CF_4$. When a diluent is used, the perfluoroalkylvinylether/diluent volume ratio is, e.g., comprised within the range of from 100:1 to 1:1.

When a gaseous stream of perfluoroalkylvinylether is made to flow over a catalyst bed, its flow rate is, e.g., within the range of from 0.025 to 0.1 Nl/h per gram of catalyst.

The contact time of the reactant with the catalyst may vary over a wide range according to the method used (whether batchwise or continuous), the nature of the catalyst, the physical shape, the possible degree of dilution of the reactant, and the reaction temperature. When the process is carried out continuously over an already-activated catalyst, and under steady-state conditions, with reactant flow rates within the range of from 0.025 to 0.1 Nl/h per gram of catalyst, the contact time may range, e.g., from 10 to 90 seconds.

The catalysts of the present invention are endowed with a long activity life.

With the process of the present invention, conversions of up to approximately 99%, and selectivities of up to approximately 90% may be obtained.

The impurities present in the end product are mostly constituted by unreacted perfluoroalkylvinylether and fluorinated olefins. It is possible to remove these impurities by using conventional techniques. The fluorinated olefins may be separated by, e.g., bubbling the gaseous reaction mixture through liquid bromine: the unsaturated products turn into liquid brominated compounds, which may then be separated, e.g., by distillation.

The main advantages of the present invention may be summarized as follows:

the reaction may be carried out at lower temperatures than in the absence of a catalyst;

the reaction is very selective, and the yield in perfluoroacyl fluoride is high;

by operating at lower temperatures, the formation may be controlled and limited to the very minimum of the many by-products—in particular, perfluoroisobutene, which is very toxic—which otherwise are unavoidably formed in the pyrolytic process in the absence of a catalyst;

the end product may be freed of its more abundant impurities, i.e., from the unsaturated impurities, in a simple and efficacious way;

the catalysts are endowed with a long activity life.

In order still better to illustrate the invention, but without limiting its scope, the following examples are given:

EXAMPLE 1

In all examples, tubular reactors 250 mm long, and having an inner diameter of 10.9 mm, are used. In each test, new reactors were used.

In Example 1, an unpacked reactor of steel AISI 316 is used. The reactor is pre-heated at 600° C. under an atmosphere of $N_2$ for two hours, and is then adjusted to the controlled temperature of 380° C. Perfluoromethylvinylether is fed to the reactor. at a flow rate of 0.6 Nl/h. The leaving gases are detected by I.R. spectrophotometry and gas-mass spectrometry. They are analyzed on-line in the gas phase by gas-chromatography. After 5 minutes from the beginning of feeding, a conversion of 49.9% and a zero selectivity to perfluoropropionyl fluoride are observed.

After a further 30 minutes, the conversion is 69.5%, and the selectivity is 49.4%.

This test demonstrates the non-selectivity of the thermal process, and the formation in situ, with time, of the active catalytic species, in the presence of the reactant.

EXAMPLE 2

The process is carried out as in Example 1, inside a reactor of AISI 316 steel. The conditions shown in the Table are used. The Table reports also the results obtained.

TABLE

| Total time, minutes | 30 | 60 | 90 | 120 | 150 |
|---|---|---|---|---|---|
| Temperature, °C. | 395 | 400 | 400 | 400 | 400 |
| Conversion, % | 74.8 | 85 | 89.6 | 90.4 | 96.3 |
| Selectivity, % | 6.7 | 68.4 | 82.5 | 82.7 | 81.1 |

This test demonstrates the formation of the catalytic species, and their progressive activation, with the consequent increase in selectivity and yield.

EXAMPLE 3

The reaction is carried out inside a reactor of copper packed with copper needles having a length ranging from 1 to 10 mm. The packed reactor is thermally pretreated at 600° C. for 3 hours, under a nitrogen atmosphere. The reactor is then adjusted to the controlled temperature of 390° C., and perfluoromethylvinylether is fed to it at a flow rate of 0.6 Nl/h. The results obtained as a function of time are reported in the following Table.

TABLE

| Total time, minutes | 5 | 30 | 80 | 120 |
|---|---|---|---|---|
| Conversion, % | 55 | 83.7 | 87 | 92.3 |
| Selectivity, % | 0 | 79.6 | 81.7 | 88.2 |

EXAMPLE 4

The reaction is carried out as in Example 3, carrying out a thermal pre-treatment at 600° C., and adjusting the reactor at the controlled temperature of 395° C. before starting to feed the perfluoromethylvinylether stream. After about 120 minutes, a conversion of 98.6%, and a selectivity of 83.9% is obtained. After 8 running hours, the catalyst does not show any losses of efficiency.

EXAMPLE 5

The reaction is carried out as in Example 4, the only difference being that the thermal pre-treatment of the reactor takes place at 300° C. The same results are obtained. The impurities are constituted by $$CF_3-CF=CF_2$$

and negligible amounts of other fluorocarbons.

EXAMPLE 6

An unpacked quartz reactor is used. The reactor is preheated at 400° C. under an atmosphere of $N_2$ for half an hour, and at 350° C. for 1 hour, and is initially adjusted to the controlled temperature of 330° C. A stream of perfluoromethylvinylether is fed at the flow rate of 0.6 Nl/h.

The results obtained as a function of time and temperature are reported in the following Table.

TABLE

| Total time, minutes | 30 | 60 | 90 | 120 | 150 | 180 | 210 |
|---|---|---|---|---|---|---|---|
| Temperature, °C. | 330 | 330 | 350 | 370 | 370 | 380 | 380 |
| Conversion, % | 27.6 | 49.4 | 61.6 | 69.4 | 82.0 | 93.3 | 93.1 |
| Selectivity, % | 85.1 | 91.0 | 89.5 | 87.5 | 85.2 | 87.2 | 87.6 |

After 8 running hours, the catalyst does not show any loss in efficiency. The impurities are constituted by $$CF_3-CF=CF_2$$

and negligible amounts of other fluorocarbons.

EXAMPLE 7

A copper reactor packed with copper needles, as in Example 3, is used. The packed reactor is thermally pretreated at 600° C. for 3 hours, under a nitrogen atmosphere, and is then adjusted to the controlled temperature of 120° C. Through it, a mixed stream of 2 Nl/h of nitrogen, and 1 Nl/h of fluorine is fed for 2 hours. Then a stream of 2 Nl/h of fluorine of 2 hours is fed. The reactor temperature is then adjusted at 390° C., and a stream of 0.6 Nl/h of perfluoromethylvinylether is then made to flow through the reactor, with the results being obtained which are reported in the following Table.

TABLE

| Total time, minutes | 5 | 35 |
|---|---|---|
| Conversion, % | 97.5 | 96.0 |
| Selectivity, % | 55.0 | 71.0 |

This Example demonstrates that active and selective species are formed, not only in the presence of the reactant as demonstrated by Example 3, but also, alternatively, in the presence of a different fluorinating agent, such as elemental fluorine.

EXAMPLE 8

The reaction is carried out inside a glass reactor packed with sodium aluminate powder, through which a stream of perfluoromethylvinylether is fed at the flow rate of 0.6 Nl/h. The conditions used are indicated in the Table, in which also the results are reported.

TABLE

| Total time, minutes | 90 | 150 | 240 | 270 | 280 | 300 | 325 |
|---|---|---|---|---|---|---|---|
| Temperature, °C. | 250 | 300 | 300 | 300 | 330 | 340 | 350 |
| Conversion, % | 7 | 13.6 | 28.5 | 31 | 53.5 | 75 | 75.8 |
| Selectivity, % | 0 | 0.4 | 49.6 | 51 | 57 | 59 | 61 |

EXAMPLE 9

A tubular reactor of AISI 316 steel, 250 mm long and having an inner diameter of 10.9 mm, is filled with 30 g of anhydrous MgF$_2$, the particles of which have a diameter within the range of from 0.7 to 1.5 mm. The reactor is heated to, and kept at the temperature of 400° C., and, under atmospheric pressure, through it a continuous stream of 0.6 Nl/h of perfluoromethylvinylether is passed. After one hour, the leaving gases, analyzed by gas-chromatography, I.R. spectrophotometry and mass spectrometry, are shown to be constituted by perfluoropropionyl fluoride (82 mol %), perfluoromethylvinylether (3%), hexafluoropropene (5%), and small amounts of other fluorocarbons, each present in an amount lower than, or equal to, 1%.

The conversion is 97%, the selectivity 85%. After more than 40 running hours, the catalyst still remained totally efficient.

EXAMPLES 10-12

By operating inside the reactor of Example 9, and following the same procedures of that Example, except for those as specifically described, the isomerization of perfluoromethylvinylether to perfluoropropionyl fluoride is carried out by using the catalysts and the operating parameters as reported in the following Table.

TABLE

| Example No. | Catalyst | Flow Rate Nl/h | Temperature inside the Reactor | Conversion after 1 hr. % | Selectivity after 1 hr. % |
|---|---|---|---|---|---|
| 10 | MgF$_2$ | 0.6 | 390° C. | 93 | 86 |
| 11 | MgF$_2$ | 0.6 | 420° C. | 99 | 75 |
| 12 | KF | 0.45 | 360° C. | 94 | 56 |

EXAMPLE 13

As the catalyst, MgF$_2$ is used.

Through the reactor of Example 9, maintained at a temperature of 380° C., a stream of CF$_3$CF$_2$—O—CF=CF$_2$ is fed at a flow rate of 0.25 Nl/hour, under atmospheric pressure.

After 1 running hour, the gases leaving the reactor, analyzed as in Example 1, are shown to contain 90% of CF$_3$CF$_2$CF$_2$COF, and traces of CF$_3$CF$_2$—O—CF=CF$_2$, the balance being essentially constituted by CF$_3$CF=CF$_2$.

The conversion is 99% and the selectivity is about 90%.

What is claimed is:

1. Process for the preparation of a perfluoroacyl fluoride wherein the acyl radical is a propionyl or butyryl group, characterized in that a perfluoroalkylvinylether, wherein the alkyl radical is a methyl or an ethyl group, is thermally treated in the presence of a catalyst selected from the group consisting of:
   (A) a fluoride of Li, Na, K, Cs or Rb, or another compound of Li, Na, K, Cs or Rb which is easily fluorinatable under the reaction conditions;
   (B) a fluoride of Be, Mg, Ca, Sr, or Ba, or another compound of Be, Mg, Ca, Sr, or Ba which is easily fluorinatable under the reaction conditions;
   (C) a fluoroaluminate, fluorosilicate, fluorotitanate or fluorometallate of an alkali metal, or of a metal belonging to group IIA of the Periodic Table, or another compound which is easily fluorinatable to yield one of the above said fluoroaluminates, fluorosilicates, fluorotitanates or fluorometallates under the reaction conditions;
   (D) a fluoride of a metal of the first transition series, or the corresponding metal, or another compound of such a metal which is easily fluorinatable under the reaction conditions;
   (E) a fluoride of a lanthanide, or the corresponding metal or another compound of such a metal which is easily fluorinatable under the reaction conditions; and
   (F) an oxyfluoride of Si, Al, Ti, Ge, Sn or Pb, or another compound of Si, Al, Ti, Ge, Sn or Pb which is easily fluorinatable to yield one of the above-said fluorides under the reaction conditions.

2. Process according to claim 1, characterized in that the compound of Li, Na, K, Cs or Rb, which is easily fluorinatable under the reaction conditions, is an oxide, a hydroxide or a oxyhalide.

3. Process according to claim 1, characterized in that the compound of Be, Mg, Ca, Sr, or Ba, which is easily fluorinatable under the reaction conditions, is an oxide, a hydroxide or a oxyhalide.

4. Process according to claim 1, characterized in that the fluoroaluminate, the fluorosilicate, the fluorotitanate, the fluorometallate belonging to group IIA of the Periodic Table, is selected from the group consisting of $K_3AlF_6$, $Cs_3AlF_6$, $K_2SiF_6$, $Cs_2SiF_6$, $CsCuF_3$, $KCuF_3$ and $CsNiF_3$.

5. Process according to claim 1, characterized in that the fluoride of a metal of the first transition series is selected from the group consisting of $CuF_2$, $NiF_2$, $ZnF_2 CoF_2$, $CoF_3$, $CrF_3$, $MnF_2$, $FeF_2$ and $FeF_3$.

6. Process according to claim 1, characterized in that the metal of the first transition series is selected from the group consisting of Cu, Ni, Zn, Cr, Mn, Fe and Co.

7. Process according to claim 6, characterized in that the metal of the first transition series is copper.

8. Process according to claim 1, characterized in that the fluoride of a lanthanide is selected from the group consisting of $LaF_3$ and $CeF_4$.

9. Process according to claim 1, characterized in that the compound of Si, Al, Ti, Ge, Sn or Pb which is easily fluorinatable to yield the oxyfluoride under the reaction conditions is an oxide or an oxide-hydroxide.

10. Process according to claims 1, 2, 3, 6, 7 or 9, characterized in that the metal or the compound which is easily fluorinatable under the reaction conditions is fluorinated in situ under the action of the perfluoroalkylvinylether or of another fluorinating agent.

11. Process according to claim 10, characterized in that the other fluorinating agent is fluorine or hydrofluoric acid.

12. Process according to claim 10, characterized in that the catalyst obtained by means of the in situ fluorination of the metal, or of the easily fluorinatable compound, is activated in situ in the presence of the perfluoroalkylvinylether.

13. Process according to claim 11, characterized in that the catalyst obtained by means of the in situ fluorination of the metal, or of the easily fluorinatable compound, is activated in situ in the presence of the perfluoroalkylvinylether.

14. Process according to any one of claims 1, 4, 5 or 8, characterized in that the pre-formed catalyst is activated in situ in the presence of the perfluoroalkylvinylether.

15. Process according to any one of claims 1, 6, 7, 10, 11 or 12, characterized in that the metal is subjected to a thermal treatment at temperatures within the range of from 300° to 650° C. before being fluorinated.

16. Process according to any one of claims 1, 2, 3, 9, 10, 11 or 12, characterized in that the compound easily fluorinatable under the reaction conditions is subjected to a thermal treatment at temperatures within the range of from 250° to 500° C. before being fluorinated.

17. Process according to one or more of claims 1, 6, 7, 10, 11, 12, 13 or 14, characterized in that when as the catalyst a metal of the first transition series is used, the reaction is carried out at temperatures within the range of from 300° to 500° C.

18. Process according to claim 17, characterized in that when as the catalyst Cu, Ni, Zn or Fe is used, the reaction is carried out at temperatures within the range of from 350° to 450° C.

19. Process according to one or more of claims 1, 9, 10, 11, 12, 14 or 16, characterized in that when as the catalyst an oxyfluoride of Si, Al, Ti, Ge, Sn or Pb is used, or another compound of Si, Al, Ti, Ge, Sn or Pb is used which is easily fluorinatable to one of the above-said oxyfluorides under the reaction conditions, this latter is carried out at temperatures within the range of from 250° to 400° C.

20. Process according to claim 19, characterized in that when as the catalyst fluorinated silica is used, the reaction is carried out at temperatures within the range of from 300° to 400° C.

21. Process according to one or more of claims 1, 3, 10, 11, 12, 14, 16, characterized in that when as the catalyst a fluoride of Be, Mg, Ca, Sr or Ba is used, or another compound of Be, Mg, Ca, Sr or Ba is used which is easily fluorinatable under the reaction conditions, this latter is carried out at temperatures within the range of from 300° to 450° C.

22. Process according to claim 1, characterized in that when as the catalyst magnesium fluoride is used, the reaction is carried out at temperatures within the range of from 350° to 450° C.

23. Process according to one or more of claims 1, 2, 10, 11, 12, 14 or 16, characterized in that when as the catalyst a fluoride of Li, Na, K, Cs or Rb is used, or another compound of Li, Na, K, Cs or Rb is used which is easily fluorinatable under the reaction conditions, this latter is carried out at temperatures within the range of from 300° to 450° C.

24. Process according to claim 1, characterized in that the process is carried out continuously, with a stream of perfluoroalkylvinylether being flown over or through a catalyst layer.

25. Process according to claim 1, characterized in that the perfluoroacyl fluoride is purified of its unsaturated impurities by bubbling it, in the gaseous state, through liquid bromine.

26. Perfluoropropionyl fluoride and perfluorobutyryl fluoride when obtained according to the process as defined in one of claims 1, 2, 3, 6, 7 or 9.

* * * * *